United States Patent [19]

Davies

[11] Patent Number: 5,591,854

[45] Date of Patent: *Jan. 7, 1997

[54] ENANTIOSELECTIVE SYNTHESIS OF SEVEN-MEMBERED CARBOCYCLES AND TROPANES

[75] Inventor: Huw M. L. Davies, Clemmons, N.C.

[73] Assignee: Wake Forest University, Winston-Salem, N.C.

[*] Notice: The term of this patent shall not extend beyond the expiration date of Pat. No. 5,342,949.

[21] Appl. No.: 324,106

[22] Filed: Oct. 14, 1994

[51] Int. Cl.$^6$ .......................... C07D 451/02; C07C 69/24; C07F 15/00; C07F 7/10

[52] U.S. Cl. .................... 546/14; 546/124; 546/132; 548/403; 560/120; 560/128

[58] Field of Search ...................... 546/124, 132, 546/14; 560/128, 120; 548/403

[56] References Cited

U.S. PATENT DOCUMENTS

| | | | |
|---|---|---|---|
| 5,262,428 | 11/1993 | Davies et al. | 514/304 |
| 5,288,872 | 2/1994 | Davies et al. | 546/132 |
| 5,342,949 | 8/1994 | Davies et al. | 546/124 |

OTHER PUBLICATIONS

Burgess, Kevin, et al., Asymmetric Syntheses of 2,3–Methanoamino Acids, Aug. 1994, 575–583.

Davies, Huw M. L., Stereoselective Cyclopropanations with Vinylcarbenoids, Tetrahedron Letters, vol. 30, No. 38, pp. 5057–5060, 1989, Great Britain.

Davies, Huw M. L., Highly Stereoselective 3+2 Annulations by Cyclopropanation of Vinyl Ethers with Rhodium(II)–Stabilized Vinylcarbenoids Followed by A Formally Forbidden 1,3–Sigmatropic Rearrangement, The Journal of Organic Chemistry, 1992, vol. 57, pp. 3186–3190.

Davies, Huw M. L., Tandem Cyclopropanation/Cope Rearrangement: A General Method for the Construction of Seven–Membered Rings, Tetrahedron vol. 49, No. 24, pp. 5203–5223, 1993, Great Britain.

Davies, Huw M. L., α–Hydroxy Esters as Inexpensive Chiral Auxiliaries in Rhodium(II)–Catalyzed Cyclopropanations with Vinyldiazomethanes, Tetrahedron Letters, vol. 32, No. 45, pp. 6509–6512, 1991, Great Britain.

Davies, Huw M. L., α–Hydroxy Esters as Chiral Auxiliaries in Asymmetric Cyclopropanations by Rhodium(II)–Stabilized Vinylcarbenoids, Journal of the American Chemical Society, 1993, 115, pp. 9468–9479.

Davies, Huw M. L., Enantioselective Syntheses of Tropanes by Reaction of Rhodium–Stabilized Vinylcarbenoids with Pyrroles, Tetrahedron Letters, vol. 33, No. 46, pp. 6935–6938, 1992.

Davies, Huw M. L., Enantioselective Synthesis of Vinylcyclopropanes by Rhodium (II)Catalyzed Decomposition of Vinyldiazomethanes in the Presence of Alkenes, Tetrahedron Letters, vol. 34, No. 45, pp. 7243–7246, 1993, Great Britain.

*Primary Examiner*—Alan L. Rotman
*Attorney, Agent, or Firm*—Zarley, McKee, Thomte, Voorhees & Sease

[57] ABSTRACT

A process of enantioselective synthesis of seven-membered carbocycles in the presence of di-rhodium(II) tetracarboxylate catalysts.

3 Claims, No Drawings

5,591,854

ENANTIOSELECTIVE SYNTHESIS OF SEVEN-MEMBERED CARBOCYCLES AND TROPANES

GRANT REFERENCE

This invention was made with government support under CHE-902428 awarded by the National Science Foundation. The government has certain rights in the invention.

BACKGROUND OF THE INVENTION

In recent times it has become known that many chiral drug compounds which have a high degree of biological activity, in fact represent racemic mixtures of optical isomers, one isomer usually being highly active, and the others not nearly as active. In some cases, only one isomer is active. As this has been discovered, it has become more desirable to prepare certain known biologically active compounds by enantioselective synthesis. Put another way, a synthesis which would provide selectively in predominant form a high percentage of one isomer over another is now an important tool for the drug synthesis chemist.

Earlier work of Dr. Huw M. L. Davies, has reported on synthesizing biologically active tropane derivatives, see for example U.S. Pat. No. 5,262,428 issued Nov. 16, 1993 concerning tropane derivatives which may be described as cocaine analogs, useful as cocaine replacement drugs. Similarly, Davies, et al., U.S. Pat. No. 5,342,949, issued Aug. 30, 1994, describes a two-step process for preparing biologically active tropane derivatives. Finally, Davies, et al., U.S. Pat. No. 5,288,872, issued Feb. 22, 1994, describes compounds for treatment of neurodegenerative diseases that contain tropane rings. The disclosures of each of these earlier patents are incorporated herein by reference.

Since seven-membered carbocycles are known to be biologically active, and many are known to be chiral, it necessarily follows that it would be important to develop a chiral synthesis of these compounds. In an earlier report by Davies and Hutcheson, *Tetrahedron Letters*, Vol. 34, No. 45, pp. 7243–7246, 1993, Dr. Davies, et al. report an effective chiral catalyst for the asymmetric cyclopropanation of alkenes. In that process as there described, enantioselective transformations are prepared by rhodium(II)-N-(arenesulfonyl) prolinate catalyzed decomposition of vinyldiazomethanes in the presence of alkenes. The enantioselectivity reported there varies from 9% up to 95%.

Earlier work, however, has demonstrated that there is little predictability of the extension of work with one chiral catalyst to another system. Put another way, experience has shown that it is not at all predictable that a chiral catalyst used in a system as for example shown in the *Tetrahedron Letters* publication necessarily works in a different system.

In accordance with the present invention, and as a further improvement on the processes reported in the earlier Davies publications and patents, it has now been discovered that a highly stereoselective synthesis of seven-membered carbocycles will occur by reacting a diene with a vinyldiazomethane, in the presence of a non-polar solvent and a di-rhodium(II) tetra[N]-arylsulfonyl 1-aza-cycloalkane-2 carboxylate. Surprisingly, the amount of enantiomeric excess (% ee) in certain instances is as high as 90%, and reaction yields may go as high as 70% to 98%.

Accordingly, it is a primary object of the present invention to provide a simple stereoselective single-step synthesis of seven-membered carbocycles.

Another object of the present invention is to provide an enantioselective process of synthesizing chiral biologically active tropane ring containing compounds.

The method and means of accomplishing each of the above objectives will become apparent from the detailed description of the invention which follows hereinafter.

SUMMARY OF THE INVENTION

Rhodium(II)(S)-(N-p-(tertbutyl)phenylsulfonyl)prolinate catalyzed decomposition of vinyldiazomethanes occurs in the presence of dienes, preferably in the presence of a non-polar solvent and results in a tandem cyclopropanation/Cope rearrangement, leading to a general enantioselective approach for the construction of seven-membered carbocycles, including tropanes.

DETAILED DESCRIPTION OF THE INVENTION

The process of the invention may be described in equation form by reaction scheme 1 as written below.

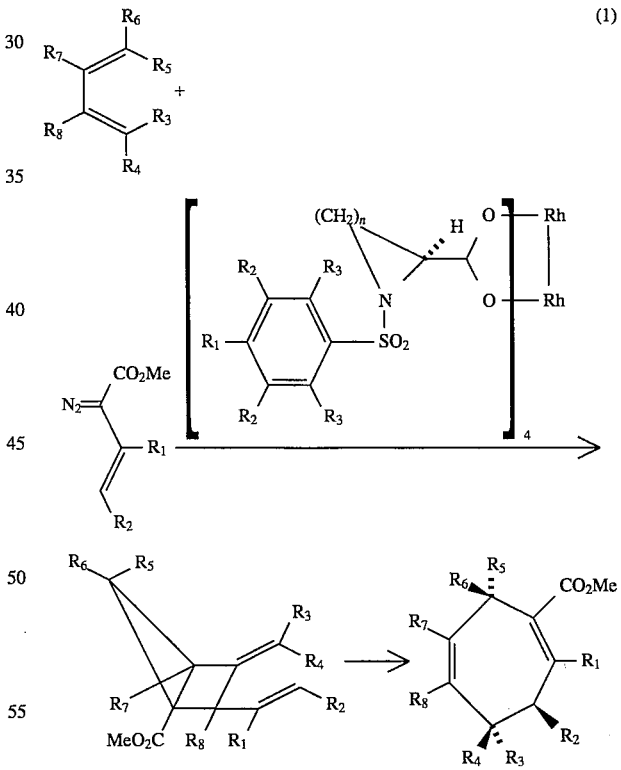

In word description a diene is reacted with a vinyldiazomethane in the presence of a non-polar solvent and a di-rhodium tetra[N-arylsulfonyl 1-aza-cycloalkane-2 carboxylate to provide a cyclopropanation product. It undergoes an immediate Cope rearrangement to a seven-membered carbocycle. In the instance where $R_3$ and $R_5$ are joined, for example by an N moiety, the resulting product is a tropane ring system.

The diene, as shown in reaction scheme 1, is represented by the following formula:

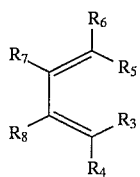

In the diene formula $R_4$ may represent hydrogen, alkyl, broadly $C_1$ to $C_{20}$ alkyl, and most preferably $C_1$ to $C_8$ alkyl. It may also be the corresponding alkoxy or acetoxy or O-siloxy. $R_6$ may be the same or different from $R_4$ and can be selected from the same groups. $R_3$ and $R_5$ can be the same as $R_4$ or preferably if one is forming a tropane ring system, they are a joining moiety, such as —[NH]— (pyrrole), an —[O]— (furan), a methylene group (cyclopentadiene), an ethylene group (cyclohexadiene) or —[CH═CH]— (benzene ring). The diene may be substituted at $R_7$ or $R_8$ if desired. If so, the groups may be the same as $R_4$ or they may be simply each or all hydrogen moieties. The vinyldiazomethane is illustrated in scheme 1 and has the following formula:

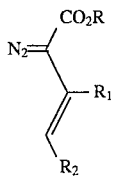

Other ester moieties other than the methyl ester ($R═CH_3$) moiety as shown in the vinyldiazomethane can be employed; however, the methyl ester provides the best results in terms of electron withdrawing and stereoselective preparation of the chiral biologically active seven-membered ring compounds. $R_1$ and $R_2$ may be the same or different and may be hydrogen, methyl, phenyl, vinyl, siloxy, ethyl ester, etc.

The catalyst, as shown in reaction scheme 1, is represented by the following formula:

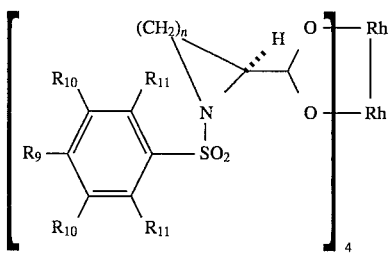

In the catalyst formula n can be 2, 3, or 4, and most preferably 3. $R_9$ can be hydrogen, tertbutyl, n-dodecyl, alkyl, broadly $C_1$ to $C_{20}$ alkyl, methoxy, nitro, and most preferably a long chain alkyl or tertbutyl. $R_{10}$ can be hydrogen, trifluoromethyl and alkyl, broadly $C_1$ to $C_{20}$ alkyl, and most preferably hydrogen. $R_{11}$ can be hydrogen, isopropyl, broadly $C_1$ to $C_{20}$ alkyl, and most preferably hydrogen.

As shown in reaction scheme 1, the reaction is conducted in the presence of a catalytically effective amount of a di-rhodium(II) tetracarboxylate catalyst, or specifically, a dirhodium(II) tetra[N]arylsulfonyl-1-aza-cyclo-2-carboxylate.

The most effective catalysts are dirhodium(II) tetrakis((S)-N-(p-terbutylbenzenesulfonyl)prolinate)($Rh_2$(S-TBSP)$_4$) and dirhodium(II) tetrakis((S)-N-(p-(n-dodecyl)benzenesulfonyl)prolinate) and their enantioners.

The amount of the catalyst can vary. Generally, a catalytically effective amount is required and satisfactory amounts are within the range of 0.0001 equivalents of vinyldiazomethane to 0.1 equivalents of the diazomethane with 0.01 equivalents being preferred. Indeed, one of the important aspects of the present invention is that only small amounts of the catalyst are required to produce the stereoselective reaction products herein described.

The reaction is preferably conducted in the presence of a non-polar solvent with a preferred solvent being selected from the group of pentane, hexane, benzene and toluene. If the reaction is not conducted in the presence of a non-polar solvent, enantiomeric purity suffers badly.

The reaction may be conducted at from 0° C. to room temperature, but the Cope rearrangements seem to occur most successfully at around 10° C., and so this is a preferred temperature. Reaction time is not critical, and may occur over from 5 minutes to 30 minutes with preferred continual stirring of the reaction.

The amount of the reactants employed can be described as at least one equivalent of vinyldiazomethane with from 1 equivalent to 20 equivalents of the diene. Thus the amount of the reactants for highest yield must be at least equimolar, but excess amounts of the diene reactant may be employed without harm.

The following examples are offered to further illustrate but not limit the process of the present invention.

EXAMPLES

The first series of experiments focused on the reaction of 2-diazobutenoates with cyclopentadiene. $Rh_2$(S-TBSP)$_4$ catalyzed decomposition of the methyl ester 1a in the presence of cyclopentadiene using pentane as solvent gave the bicyclo[3.2.1]octadiene 2a in 63% ee. The enantioselectivity of this process was determined by GC on a Chiraldex β-PH cyclodextrin column and confirmed by NMR using tris[3-(heptafluoro-propylhydroxymethylene)-(−)-camphorato praseodymium(III) as a chiral shift reagent. A similar reaction with the tert-butyl ester 1b gave the bicyclo [3.2.1]octadiene 2b in only 5% ee. This dramatic drop in enantioselectivity parallels the results that were observed in the cyclopropanation of styrene. The detrimental effect of a bulky ester group in this system is in contrast to the trend that is seen in chiral copper and rhodium amide catalyzed decomposition of diazoacetates where bulky esters strongly enhance asymmetric induction. These reactions are represented by the scheme shown below.

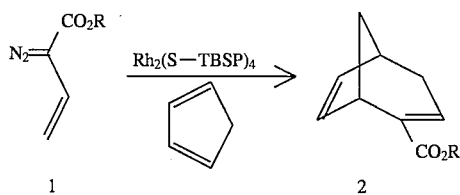

The studies were then focused on the effect of structural variations within the vinylcarbenoid upon the level of asymmetric induction. The results of these studies are summarized in Table 1. The exclusive formation of the endo relative stereochemistry for the bicyclo[3.2.1]octadienes 2c-g,j was readily established on the basis of the coupling constants at the bridgehead proton and is fully consistent with the boat transition state required for the Cope rearrangement of divinylcyclopropanes. Several modifications to the vinyldiazomethanes at either of the vinyl positions were tolerated as seen for 1c–1h (64–91% ee). Introduction of vinyl, phenyl or methyl functionality at the vinyl terminus (1c–e) resulted in significantly higher levels of asymmetric induction. However, the presence of a siloxy group adjacent to the carbenoid (1i, 42% ee) or a strongly electron withdrawing group at the vinyl terminus (1j, 10% ee) resulted in a large decrease in asymmetric induction.

TABLE 1

$Rh_2(S-TBSP)_4$ catalyzed decomposition of vinyldiazomethanes 1 in the presence of cyclopentadiene

| compound | R | $R_1$ | $R_2$ | ee, % | yield, % |
|---|---|---|---|---|---|
| a | Me | H | H | 63 | 76 |
| b | tBu | H | H | 5 | 50 |
| c | Me | H | CH=CH$_2$ | 91 | 64 |
| d | Me | H | Me | 83 | 75 |
| e | Me | H | Ph | 75 | 92 |
| f | Me | cyclo(CH$_2$)$_3$ | | 68 | 68 |
| g | Me | cyclo(CH$_2$)$_4$ | | 69 | 70 |
| h | Me | Me | H | 64 | 66 |
| i | Me | OTBDMS | H | 42 | 66 |
| j | Et | H | CO$_2$Et | 10 | 98 |

The wider application of $Rh_2(S-TBSP)_4$ for the enantioselective formation of seven-membered carbocycles was established through the reaction of the vinyldiazomethane 1e with a variety of dienes (eqs. 4–7). With 2,5-dimethylfuran, reaction of 1e gave 3 in 86% ee. Such high levels of asymmetric induction were repeated with acyclic dienes. For example, reaction of 1e with trans-piperylene resulted in the formation of the cis-cycloheptadiene 4 in 90% ee. In addition to the absolute stereocontrol, this reaction proceeds with excellent control of regiochemistry and relative stereochemistry. Cyclopropanation occurs exclusively at the least substituted double bond and the relative stereochemistry is fixed by the demands of the boat transition state for the Cope rearrangement. The enantioselectivity of this reaction was repeated for the corresponding conversion of cis-piperylene to the trans-cycloheptadiene 5, and the reaction of 1e with trans-1-(tert-butyldimethylsiloxy)butadiene led to the formation of cis-cycloheptadiene 6 in 85% ee.

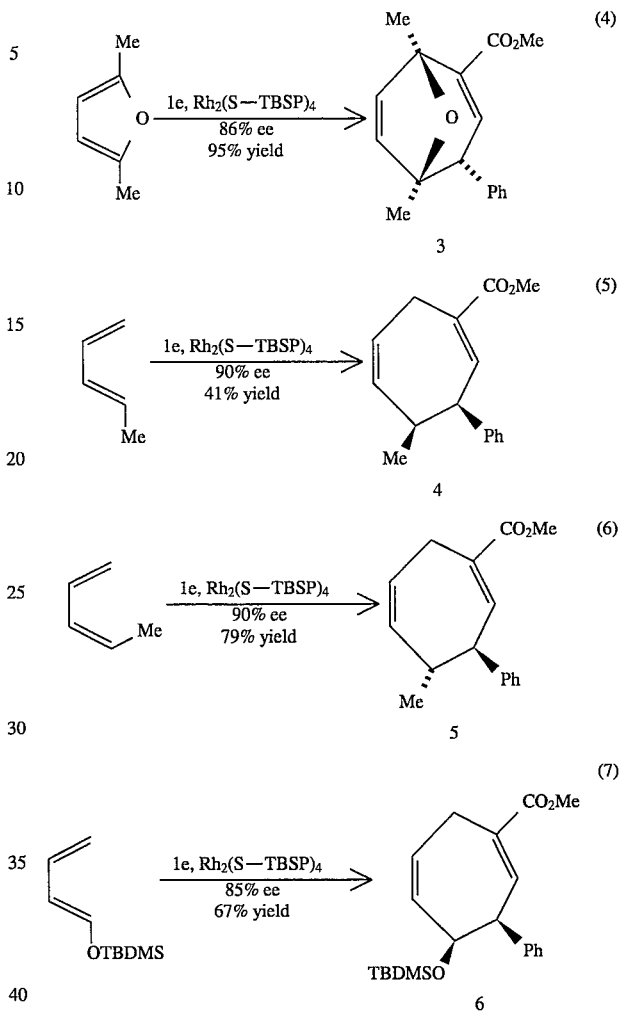

The specific application of $Rh_2(S-TBSP)_4$ for the enantioselective formation of tropanes was established through the reaction of the vinyldiazomethane 1a with a variety of pyrroles (Table 2). With N-(terbutoxycarbonyl)pyrrole, reaction of 1a gave 7a in 51% ee. The extent of asymmetric induction was variable but two main trends were observed. The highest enantioselectivity was obtained when the N-substituent was bulky and moderately electron withdrawing. Significantly lower enantioselectivities were obtained when the N-substituent was strongly electron withdrawing as seen for 7b and 7d. As 7a has been converted to anhydroecgonine methyl ester (Davies, H. M. L.; Saikali, E.; Young, W. B. J. Org. Chem. 1991, 56, 5696), a compound that is a very important building block for the synthesis of biologically active tropane derivatives. The reactions shown in Table 2 represent a general approach for the enantioselective synthesis of tropanes.

TABLE 2

Rh$_2$(S—TBSP)$_4$ catalyzed decomposition of vinyldiazomethane 1a in the presence of pyrroles 7

| PRODUCT | R$_{12}$ | ee, % | YIELD, % |
|---|---|---|---|
| 7a | CO$_2$tBu | 51 | 50 |
| 7b | COMe | 17 | 46 |
| 7c | CO$_2$Me | 42 | 44 |
| 7d | SO$_2$Me | 29 | 34 |

The studies were then focused on what structural features of the catalyst were necessary for enantioselective reactions. This was achieved using the reaction between 1d and styrene as a model reaction and the results are summarized in Tables 3 and 4. The results in Table 3 demonstrate that a wide range of aromatic functionality may be substituted on the sulfonyl group without extreme loss of enantioselectivity. The preferred catalysts are the para(terbutyl)phenyl and the para(n-dodoceyl)phenyl sulfonyl derivatives, as these catalysts are soluble in pentane and this solvent leads to significantly higher levels of asymmetric induction than the more commonly used solvent, dichloromethane.

In table 4, the effect on asymmetric induction of more extensive alterations to the catalysts are reported. Low enantioselectivities were obtained with catalysts containing an alkyl sulfonyl derivative or acyclic ligands. However, very high levels of enantioselectivity (81% ee in each case) were obtained when the five-membered ring of the prolinate catalyst was changed to either a four or six-membered ring. Therefore, it may be concluded that the ideal rhodium(II) catalysts are N-arylsulfonylprolinate derivatives or other N-arylsulfonyl-1-azacycloalkane-2-carboxylates that have sufficient solubility to allow the catalytic process to be carried out in non-polar solvents such as pentane. As both D- and L-proline are readily available, these processes would allow enantioselective synthesis of either enantiomer of the seven-membered ring products.

TABLE 3

Effect of aryl functionality on enantioselectivity with rhodium(II) prolinate catalysts

| Ar | ee, % | Ar | ee, % |
|---|---|---|---|
| C$_6$H$_5$ | 74 | 4-C$_{12}$H$_{25}$-C$_6$H$_4$ | 79 (94) |
| 4-MeO-C$_6$H$_4$ | 76 | 3,5-(CF$_3$)$_2$-C$_6$H$_3$ | 75 |
| 4-O$_2$N-C$_6$H$_4$ | 83 | 2,4,6-$^i$Pr$_3$-C$_6$H$_2$ | 61 |
| 4-$^t$Bu-C$_6$H$_4$ | 74 (90) | | |

TABLE 4

Effect of catalyst structure on enantioselectivity

| Rh$_2$L$_4$ | ee, % | Rh$_2$L$_4$ | ee, % |
|---|---|---|---|
| [prolinate, SO$_2^i$Pr] | 30 | [prolinate, SO$_2$(4-$^t$BuPh)] — 4-membered ring | (81) |

TABLE 4-continued

Effect of catalyst structure on enantioselectivity

[Reaction scheme: Ph-CH=N₂ + Ph-CH=CH-C(=CH-OMe)(OMe) → cyclopropane product, catalyzed by Rh₂L₄ in CH₂Cl₂ (or pentane)]

Id

| Rh₂L₄ | ee, % | Rh₂L₄ | ee, % |
|---|---|---|---|
| [iPr, H, N-SO₂(4-tBuPh), O-Rh-O-Rh]₄ | 30 | [piperidine-H, N-SO₂(4-tBuPh), O-Rh-O-Rh]₄ | (81) |
| [PhCH₂, H, N-SO₂(4-MePh), O-Rh-O-Rh]₄ | 6 | | |

In summary, Rh₂(S-TBSP)₄ catalyzed decomposition of vinyldiazomethanes in the presence of dienes results in a general and enantioselective entry to seven-membered carbocycles. The utility of this process is underscored by the high enantioselectivity observed in these studies combined with the predictable control of regiochemistry and diastereoselectivity of the tandem cyclopropanation/Cope rearrangement.

Next, the effect of ester functionality on enantioselectivity was tested, and in particular, the methyl ester group of the vinyldiazomethane was replaced with other R groups and a trend was noticed that as the size of the R group increased, there was a decrease in selectivity. Thus, methyl ester moieties are preferred, but one may be able to use ethyl, propyl, isopropyl or utilize butyl, isobutyl or tert-butyl as well. Beyond the butyl moiety for the vinyldienes methane ester group, the amount of selectivity is so decreased one would not want to use such larger moieties in the reaction.

In these examples, dry solvents were obtained by the following means: ether, THF and hexane were distilled from sodium benzophenone ketal under Ar; methylene chloride was distilled over calcium hydride under Ar. All other solvents were dried sufficiently by storage over 4 Å molecular sieve. Petroleum ether refers to that fraction boiling in the range 40°–60° C. Flash chromatography was carried out by the method of Still on silica gel (Grade 60, 230–400 mesh). $^1$H and $^{13}$C NMR spectra were recorded for solutions in CDCl₃ at 200 and 50.3 MHz respectively on a Varian VXR200 instrument. Chemical shifts are quoted in ppm relative to TMS. Rhodium(II) N-(tert-butylbenzenesulfonyl)prolinate 3, see Davies, H. M. L.; Bruzinski, P. R.; Hutcheson, D. K.; Fall, M. J.; Huby, N. J. S., in preparation, methyl 2-Diazobutenoate, see Davies, H. M. L.; Hougland, P. W.; Cantrell, W. R., Jr. *Synth. Commun.* 1992, 22, 971, N-BOC-pyrrole, see Grehn, L.; Ragnarsson, U. *Angew. Chem. Int. Ed. Engl.* 1984, 296, N-acetylpyrrole, see Reddy, G. S. Chem. and Ind., 1965, 1426, N-methoxycarbonylpyrrole, see Acheson, R. M.; Vernon, J. M. *J. Chem. Soc.* 1961, 457, and N-methylsulfonylpyrrole, see Prinzbach, H.; Kaupp, G.; Fuchs, R.; Joyeux, M.; Kitzing, R.; Markert, J. *Chem. Ber.*, 1973, 106, 3824, and racemic methyl 8-1,1-dimethylethoxycarbonyl)-8-azabicyclo[3.2.1]octa-2,6-diene-2-carboxylate 7a, see Saikali, E., Ph.D. Thesis, Wake Forest University, 1992, were prepared by literature procedures.

Methyl Bicyclo [3,2,1]octa-2,6-diene-2-carboxylate
(2a)

A solution of 1a (0.15 g, 1.2 mmol) in pentane (20 mL, dry) was added to a stirred mixture of rhodium (II) N-(benzensulfonyl)(L)prolinate (0.00787 g, 0.006 mmol, 0.8%) and cyclopentadiene (0.4 g, 6x, 6 mmol) in pentane (30 mL, dry) at room temperature over 20 min under argon. After stirring overnight, the solvent was removed under reduced pressure. Purification of the product by chromatography on silica gel using pet ether/ether (5:1) as eluent gave 2a as white gel (0.15 g, 76%)e:
$^1$H-NMR (CDCl₃):δ6.51 (m,1H), 6.25 dd,J=5.5,2.8,1H), 5.75 (dd,J=5.5,2.8 Hz, 1H), 3.69 (s,3H), 3.32 (m, 1H), 2.72 (m, 1H), J=2.45 (ddd, J=22.0, 4.1, 3.0 Hz, 1H), 2.05 (m, 1H), 1.94 (d,d J=20.0, 4.1 Hz, 1H), 1.60 (d, J=9.0 Hz, 1H). $^{13}$C-NMR (CDCl₃); δ165.4, 139.4, 139.2, 136.6, 131.1, 51.7, 39.8, 37.8, 37.1, 29.6, 28.6. IR (neat): 3056.7, 2947.3, 1711.2, 1436.0, 1248.3, 1082.1, 945.9, 906.4, 697.7 cm⁻¹. MS m/e (relative intensity): 164 (44), 149 (4), 132 (38), 105 (61), 91 (8), 77 (36), 51 (16). Retention time on GC: (chiraldex B-PH cyclodextrin column) A, 32.15; B, 32.87, 43.47 min, calculated ee % (A):63% (Initial oven temp. 95° C., rate 0.5° C. (C./min), final temp. 105° C., flow rate, 0.8 mL/min, carrier gas, He).

tert-Butyl bicyclo[3,2,1] octa-2,6-diene-carboxylate
(2b)

A solution of 1b (0.36 g, 2.14 mmol) in pentane (20 mL, dry) was added to a stirred mixture of rhodium (II) N-(benzensulfonyl)(L) prolinate (0.0193 g, 0.00168 mmol, 0.8%) and cyclopentidiene (0.707 g, 5x. 10.7 mmol) in pentane (30 mL, dry) at room temperature over 20 min. under argon. After stirring overnight, the solvent was removed under reduced pressure. The product was purified by chromatography on silica gen using pet ether/ether (4:1) as eluentto guve 2b as a white gel (0.22 g, 50%): $^1$H-NMR (CDCl₃)δ6.42 (br, 1H), 6.25 (dd, J=5.5, 2.8 Hz, 1H), 5.85 (dd, J=5.5, 2.8 Hz, 1H), 3.29 (b, 1H), 2.72 (br m, 1H), 2.45 (ddd, J=22.0, 4.1, 3.0 Hz, 1H), 2.05 (m, 1H), 1.98 (dd, J=20.0, 4.1 Hz, 1H), 1.62 (d, J=9.0 mHz, 1H), 1.5 (s, 9H). $^{13}$C-NMR (CDCl₃):δ165.4, 139.6, 139.0, 134.9, 130.8, 79.8, 40.0, 37.8, 37.2, 28.6. IR (neat): 5057.9, 2979.0, 2837.5, 1686.5, 1627.2, 136.9, 1303.6, 1259.1, 1162.1, 918.0, 747.3, 732.5 cm⁻¹. MS m/e: (relative intensity): 206 (46), 150 (97), 132 (58), 105 (105), 104 (80), 91 (30), 77 (55), 57 (94), 51 (24). Anal. Calcd for C13H18 O2: C, 75.68; H, 8.8, Found: C, 75.62; H, 8.82. Retention time on GC: (chiraldex B-PH cyclodextrin column) A, 34.21; B, 34.72 min, calculated ee % (A): 5% (Initial oven temp. 100° C., rate 0.3° C. (C./Min), final temp. 100° C., flow rate, 0.8 mL/min, carrier gas, He).

Methyl 4-vinylbicyclo[3,2,1]octa-2,6-diene-2-carbonxylate
(2c)

A solution of 1c (0.15 g, 1.0 mmol) in pentane (20 mL, dry) was added to a stirred mixture of rhodium (II) N-(benzensulfonyl) (L) prolinate (0.0092 g, 0.008 mmol, 0.8%) and cyclopentadiene (0.33 g, 5x, 5 mmol) in pentane (30 mL, dry) at room temperature over 20 min under argon. After stirring overnight, the solvent was removed under reduced pressure. Purification of the product by chromatography on silica gel using pet ether/ether (50:1) as eluent gave 2c as white gel (0.12 g, 64%). Slightly isomerization to conjugated vinyl (15%) was observed after chromatography on silica gel. $^1$H-NMR (CDCl$_3$);δ6.40 (br, 1H), 6.43 (dd, J=5.6, 2.9 Hz, 1H), 5.71 (d, J=11.0 Hz, 1H), 3.72 (s, 3H), 3.25 (br, 1H), 3.15 (br, 1H), 2.89 (br, 1H), 21.7 (m, 1H), 1.80 (d, J=Hz, 1H). $^{13}$C-NMR (CDCl$_3$):δ163.5, 143.2, 141.1, 137.1, 134.0, 132.6, 130.1, 58.9, 56.7, 52.1, 43.3, 38.6. MS m/e (relative intensity); 190 (112), 175 (290), 158 (111), 143 (56), 131 (932), 129 (410), 115 (353), 103 (118), 91 (630), 77 (252), 65 (187), 51 (180), IR (neat): 2950.4, 1738.1, 1603.2, 1445.2, 1397.4, 1256.1, 1161.8, 925.9, 911.2, 894.7, 770.9, 655.4 cm$^{-1}$. HRMS for $C_{12}H_{14}O_2$; calcd, 190.09937; found, 190.09829. Retention time on GC: (chiraldex B-PH cyclodextrin column) A, 57.50; B, 57.94 min, calculated ee % (A): 41% (Initial oven temp. 100° C., rate 0.4 (C./Min), final temp. 120° C., flow rate, 0.8 mL/min, carrier gas, He).

Methyl 4-methylbicyclo[3,2,1] octa-2,6-diene-2-carboxylate (2d)

A solution of 1d (0.76 g, 5.47 mmol) in pentane (20 mL, dry) was added to a stirred mixture of rhodium (II) N-(benzensulfonyl)(L) prolinate (0.035 g, 0.082 mmol, 0.8%) and cyclopentadiene (1.4 g, 5x, 20.7 mmol) in pentane (30 mL, dry) at room temperature over 20 min under argon. After stirring overnight the solvent was removed under reduced pressure. Purification of the product by chromatography on silica gel using per ether/ether (8:1) as eluent gave 2d as white gel (0.73 g, 75%): $^1$H-NMR (CDCl$_3$)δ6.39 (dd, J=5.6, 2.9 Hz, 1H), 6.34 (br, 1H), 5.68 (dd,J=5.6, 2.8 Hz, 1H), 3.74 (s, 3H), 3.31 (br, 1H), 2.77 (br m, 1H), 2.57 (dq, J=4.1, 6.7 Hz, 1H), 2.15 (m, 1H), 1.78 (d, J=9.0 Hz, 1H), 0.98 (d, 6.7 Hz, 3H). $^{13}$C-NMR (CDCl$_3$):δ167.1, 157.6, 139.5, 130.1, 115.4, 50.9, 40.6, 38.8, 38.2, 35.2, 25.7, 25.6, 18.3. IR (neat): 3062.5, 2962.4, 2870.3, 1716.7, 1695.8, 1627.5, 1446.8, 1310.8, 1276.3, 1237.1, 1097.9, 1096.3, 939.8, 640.0, 672.6 cm$^{-1}$. MS m/e (relative intensity): 178 (60), 146 (81), 119 (170), 105 (48), 103 (77), 91 (350), 77 (134), 65 (113), 51 (94).

Anal. for $C_{11}H_{14}O_2$: Calcd: C, 74.12; H, 7.92. Found: C, 73.89; H, 7.9. Retention time on GC: (chiraldex B-PH cyclodextrin column) A, 40.92; B, 41.22, min, calculated ee % (B): 88% (Initial oven temp, 85° C., rate 0.4 (C/Min), final temp. 98° C., flow rate, 0.8 mL/min, carrier gas, He).

Methyl endo-4-phenyl-bicyclo[3.2.1]octa-2,6-diene-2-carboxylate (2e)

A solution of 1e (0.11 g, 0.52 mmol) in dry pentane (10 mL) is added dropwise to a stirred solution of Rh$_2$(TBSP)$_4$(0.0074 g, 5.1 mmol) and freshly distilled cyclopentadiene (1.17 g, 17.6 mmol) in dry pentane (50 mL) under an argon atmosphere at room temperature. After stirring for two hours the solvent is removed under reduced pressure. Purification by silica gel column chromatography (5/95; diethyl ether/petroleum ether, R$_f$=0.26) gave the product as a yellow oil (0.12 g, 92%), IR (neat) 2949.0, 2360.1, 2340.9, 1711.9, 1261.4; $^1$H NMR (CDCl$_3$)d 7.39–7.07 (m, 5H), 6.66 (s, 1H), 6.37 (dd, 1H, J=5.7, 2.9 Hz), 5.27 (dd, 1H, J=5.7, 2.8 Hz), 3.80 (dd, 1H, J=4.4, 3.2 Hz), 3.76 (s, 3H), 3.34 (t, 1H, J=3.8 Hz), 3.04 (ddd, 1H, J=4.7. 4.6, 2.4 Hz), 2.26 (ddd, 1H, J=9.9, 4.9, 4.9 Hz), 2.00 (d, 1H, J=9.9 Hz); $^{13}$C NMR (CDCl$_3$) d 166.9, 141.1, 140.2, 139.3, 138.2, 130.5, 128.2, 127.8, 126.6, 51.7, 45.8, 44.3, 43.0, 37.8; MS m/z (relative intensity) 240 (100), 208 (11), 181 (52), 165 (25), 115 (12), 77 (7), 51 (7). (2f): A solution of 1f (0.35 g, 2.1 mmol) in pentane (20 mL, dry) was added to a stirred mixture of rhodium (II) N-(benzensulfonyl)(L) prolinate (0.0193 g, 0.0008 mmol, 0.8%) and cyclopentadiene (0.69 g, 5x, 10.5 mmol) in pentane (30 mL, dry) at room temperature over 20 min under argon. After stirring overnight, the solvent was removed under reduced pressure. Purification of the product by chromatography on silica gel using pet ether/ether (50:1) as eluent gave 2f as white gel (0.17 g, 40%): $^1$H-NMR (CDCl$_3$)δ6.35 (dd, J=5.6, 2.8 Hz, 1H), 5.64 (dd, J=5.6, 2.8 Hz, 1H), 3.73 (s, 3H), 3.20 (br, 1H), 3.0 (br 1H), 2.48–2.60 (br, 3H), 2.05 (m, 1H), 1.65–1.80 (m, 3H), 1.60 (d, J=9.0 Hz, 1H), 0.9–1.05 (m, 1H). $^{13}$C-NMR (CDCl$_3$):δ168.5, 149.8, 141.3, 130.6, 128.7, 51.2, 43.4, 42.2, 41.6, 41.0, 31.2, 30.0, 27.6, 26.1; IR (neat) 2953.3, 1734.2, 1694.1, 1197.3, 750.6, 732.8, 700.9, 663.6 cm$^{-1}$: MS m/e (relative intensity): 204 (130), 172 (156), 161 (17), 145 (150), 129 (83), 117 (91), 105 (32), 103 (32), 91 (110), 77 (63), 51 (35), HRMS for $Cl_3H_{16}O_2$: calcd, 204.1150, found: 204.1147. Retention time on GC: (the standard column*) A, 34.70; B, 36.32 min, calculated ee % (A): 68% (Initial oven temp. 130° C. rate 0.2 (C./Min), final temp. 140° C., flow rate, 0.8 mL/min, carrier gas, He). (2g): A solution of 1g (0.36 g, 2.34 mmol) in pentane (20 mL, dry) was added to a stirred mixture of rhodium (II) N-(benzensulfonyl) (L) prolinate (0.0185 g, 0.01645 mmol, 0.7%) and cyclopentadiene (0.077 g, 5x, 11.7 mmol) in pentane (30 mL, dry) at room temperature over 20 min under argon. After stirring overnight, the solvent was removed under reduced pressure. The crude $^1$H-NMR spectrum showed that there was cyclopropane still existed in the mixture. Further refluxing in benzene for 24 hr drove the reaction to completion. Purification of the product by chromatography on silica gel using pet ether/ether (50:1) as eluent gave 2g as white gel (0.25 g, 56%): $^1$H-NMR (CDCl$_3$)δ6.38 (dd, J=3.0, 5.6 Hz, 1H), 5.71 (dd, J=3.0, 5.6 Hz, 1H), 3.70 (s, 3H), 3.37 (br m, 1H), 3.1 (m, 1H), 2.55 (br m, 1H), 2.19 (br q, 1H), 2.03 (ddd, J=9.73, 4.61, 4.76 Hz, 1H), 1.75 (b m, 4H), 1.25 (b m, 3H). $^{13}$C-NMR (CDCl$_3$);δ166.6, 145.0, 141.4, 130.7, 128.8, 51.1, 43.4, 42.2, 41.6, 40.7, 31.2, 29.9, 27.5, 26.0. IR (neat): 2935.3, 2858.3, 1729.7, 1694.0, 1607.8, 1440.8, 1236.2, 1187.6, 924.9, 767.2, 732.7 cm$^{-1}$, MS m/e (relative intensity): 218 (36), 186 (19), 159 (43), 131 (19), 129 (22), 117 (31), 105 (11), 91 (40), 77 (23), 51 (11). HRMS: $C_{14}H_{18}O_2$ clcd, 218.1307; observed, 218.1304. Retention time on GC: (chiraldex B-PH cyclodextrin column) A, 42.56; B, 44.88 min, calculated ee % (A): 69% (Initial oven temp. 130° C., rate 0.3 (C./Min), final temp. 140 ° C., flow rate: 0.8 mL/min, carrier gas, He).

Methyl 3-methylbicyclo [3,2,1] octa-2,6-diene-2-carboxylate (2h)

A solution of 1h (0.208 g, 1.48 mmol) in pentane (20 mL, dry) was added to a stirred mixture of rhodium (II) N-(benzensulfonyl)(L) prolinate (0.0136 g, 0.0038 mmol, 0.8%) and cyclopentadiene (0.98 g, 10x, 14.8 mmol) in pentane (30 mL, dry) at room temperature over 20 min under argon. After stirring overnight, the solvent was removed under reduced pressure. The purification of product by chromatography on silica gel using pet ether/ether (10:1) as eluent gave 2h as white gel (0.22 g, 60%): $^1$H-NMR (CDCl$_3$):δ6.25

(dd, J=5.5, 2.8 Hz, 1H), 5.77 (dd, J=5.5, 2.8 Hz, 1H), 3.76 (s, 3H), 3.28 (br m, 1H), 2.70 (br m, 1H), 2.4 (dd, J=20.0, 4.1 Hz, 1H), 1.98 (m, 1H), 1.90 (br s, 3 H), 1.60 (d, J=9.0 Hz, 2H). $^{13}$C-NMR (CDCl$_3$):δ167.8, 145.0, 139.0, 131.0, 114.0, 51.0, 40.2, 39.6, 37.7, 35.6, 21.6. IR (neat): 2949.7, 2879.7, 1698.4, 1440.1, 1298.0, 1240.3, 1073.2, 899.0, 749.6, 707.6 cm$^{-1}$. MS m/e (relative intensity): 176 (78), 133 (115), 115 (6), 105 (115), 91 (18), 77 (61), 51 (28). Anal for C$_{11}$H$_{15}$O$_2$; Calcd; C, 74.12; H, 7.92. Found: C, 73.86; H, 7.98. Retention time on GC: (chiraldex B-PH cyclodextrin column)A, 38.2; B, 40.54 min, calculated ee % (A): 64% (Initial oven temp. 90° C., rate (C./Min), final temp. 105° C., flow rate 0.8 mL/min, carrier gas, He).

Methyl bicyclo [3,2,1] octa-2,6-diene-3-diemethyl-t-butylsilyl-carboxylate (2i)

A solution of 1i (0.9 g, 3.5 mmol) in pentane (20 mL, dry) was added to a stirred mixture of rhodium (II) N-(benzensulfonyl) (L)prolinate (0.0200 g, 0.00175 mmol, 0.5%) and cyclopentadiene (01.16 g, 5x, 17.5 mmol) in pentane (30 mL, dry) at room temperature over 20 min under argon. After stirring overnight, the solvent was removed under reduced pressure. Purification of the product by chromatography on silica gel using pet ether/ether (4:1) as eluent yielding 2i as a white gel (0.067 g, 66%): $^1$H-NMR (CDCl$_3$):δ6.30 (dd, J=5.5, 2.8 Hz, 1H), 5.74 (dd, J=5.5, 2.8 Hz, 1H), 3.70 (s, 3H), 3.44 (br m, 1H), 2.79 (br tri, 1H), 2.43 (dd, J=20.0, 4.1 Hz, 1H), 1.92 (d, J=20 Hz, 1H), 1.59 (d, J=9.0 Hz, 1H), 0.93 (s, 9H), 0.15 (s, 6H). $^{13}$C-NMR (CDCl$_3$):δ165.4, 139.6, 139.0, 134.9, 130.8, 79.8, 40.0, 37.8, 37.2, 28.6, 28.1 MS m/e (relative intensity): 196 (37), 165 (25), 137 (100), 105 (75), 79 (96), 77 (73), 59 (60). IR (neat): 3065.3, 2935.7 2859.5, 1742.2, 1675.1, 1606.0, 1367.5, 1200.9, 1125.3, 904.1, 833.0 cm$^{-1}$. Retention time on GC: (chiraldex B-PH cyclodextrin column) A, 32.15; B, 32.87, 43.47 min, calculated ee % (A): 42% (Initial oven temp. 95° C., rate 0.5° C. (C./min), final temp. 105° C., flow rate, 0.8 mL/min, carrier gas, He).

Diethyl bicyclo[3,2,1]octa-2,6-diene-2,4-dicarboxylate (2j)

A solution of 1j (0.300 g, 1.5 mmol) in pentane (20 mL, dry) was added to a stirred mixture of rhodium(II) N-(benzensulfonyl)(L) prolinate (0.0138 g, 0.012 mmol, 0.8%) and cyclopentadiene (0.495 g, 5x, 7.5 mmol) in pentane (30 mL, dry) at room temperature over 20 min under argon. After stirring overnight, the solvent was removed under reduced pressure. Purification of the product by Kugerlrohr distillation under 0.4 mmg 120° C.–140° C. gave 2j as white gel (0.35 g, 98%): $^1$H-NMR (CDCl$_3$)δ6.61 (br m, 1H), 6.39 (dd, J=5.8, 2.8 Hz, 1H), 5.67 (dd, J=5.8, 2.8 Hz, 1H), 4.0–4.30 (m, 4H), 3.45 (dd, J=4.6, 2.8 Hz, 1H), 3.25 (m, 2H), 2.21 (ddd, J=9.8, 4.8, 4.8 Hz, 1H), 1.79 (d, J=9.8, 1H), 1.28 (t, J=7.1 Hz, 3H), 1.23 (t, J=7.1 Hz, 3H). $^{13}$C-NMR (CDCl$_3$): δ170.6, 165.7, 142.6, 139.2, 132.9, 129.8, 60.7, 60.5, 43.7, 42.1, 41.1, 37.9, 14.2. IR (neat): 2983.8, 1728.4, 1694.7, 1261.2, 1190.5, 948.6, 903.5, 769.4, 748.8, 733.2, 639.2, 472.0 cm$^{-1}$. MS m/e (relative intensity): 250 (190), 204 (440), 176 (450), 148 (140), 132 (230), 131 (260), 105 (290), 103 (435), 77 (300), 51 (100). Retention time on GC: (chiraldex B-PH cyclodextrin column) A, 54.31; B, 54.97 min, calculated ee % (B): 10% (Initial oven temp. 95° C., rate 0.5 (C./Min), final temp. 105° C., flow rate, 0.8 mL/min, carrier gas, He).

Methyl endo-2,5-dimethyl-8-oxo-4-phenylbicyclo[3.2.1]octa-2,6-diene-2-carboxylate (3)

A solution of 1e (0.11 g, 0.52 mmol) in dry pentane (10 mL) is added dropwise to a stirred solution of Rh$_2$(TBSP)$_4$ (0.0079 g, 5.5 mmol) and 2,5-dimethylfuran (0.25 g, 2.6 mmol) in dry pentane (50 mL) under an argon atmosphere at room temperature. After stirring two hours the solvent is removed under reduced pressure. Purification by silica gel column chromotography (5/95; diethyl ether/petroleum ether, R$_f$=0.11) gave the product as a yellow oil (0.13 g, 95%); IR (neat) 2975.1, 1714.8, 1272.8 cm$^{-1}$; 1-H NMR (CDCl$_3$) 7.45–7.05 (m, 5H), 6.65 (ddd, 1H, J=2.6, 1.5, 1.3 Hz), 6.37 (dd, 1H, J=5.6, 2.9 Hz), 5.28 (dd, 1H, J=5.6, 2.7 Hz), 3.80 (dd 1H, J=4.4, 2.6 Hz), 3.77 (s, 3H), 3.33 (ddd, 1H, J=4.9, 2.7, 1.3 Hz), 2.00 (d, 1H, J=10.0 Hz); $^{13}$C NMR (CDCl$_3$), d 166.4, 142.3, 14.0.9, 139.2, 136.1, 131.1, 128.8, 128.3, 127.3, 87.0, 83.9, 51.5, 50.5, 23.1, 20.0; MS m/z (relative intensity) 270 (7), 211 (100), 195 (13), 167 (19), 152 (15), 115 (29), 77 (18), 51 (15); Anal. Calcd for C$_{17}$H$_{18}$O$_3$; C, 75.53; H, 6.71. Found: C, 75.40; H, 6.77.

Methyl cis-4-methyl-3-phenyl-cyclohepta-1,5-diene-1-carboxylate (racemic) (4)

A solution of 1e (0.60 g, 3.0 mmol) in dry pentane (40 mL) is added dropwise to a stirred solution of Rh$_2$(TBSP)$_4$(0.0392 g, 27.1 mmol) and trans-1,3-pentadiene (1.01 g, 14.8 mmol) in dry pentane (40 mL) under an argon atmosphere at room temperature. After stirring for two hours the solvent is removed under reduced pressure. Purification by silica gel column chromatography (1/99; diethyl ether/ petroleum ether, R$_f$=0.05) gave the product as a yellow oil (0.29 g, 41%); IR (neat) 3025.0, 2958.9, 2873.4, 1716.1, 1452.3, 1435.0, 1281.4, 1247.5; $^1$H NMR (CDCl$_3$)d 7.30–7.25 (m, 5H), 7.17 (dd, 1H, J=6.1, 1.6 Hz), 5.85–5.72 (m, 1H), 5.41 (ddd, 1H, J=12.6, 6.0, 1.6 Hz), 4.00–3.90 (m, 1H), 3.70 (s, 3H), 3.27 (d, 1H, J=7.00 Hz), 3.03–2.88 (m, 1H), 0.91 (d, 3H, J=7.2 Hz); $^{13}$C NMR (CDCl$_3$)d 168.2, 144.1, 140.4, 136.5, 131.0, 129.2, 127.9, 126.6, 126.4, 51.9, 48.8, 36.3, 25.9, 17.4; MS m/z (relative intensity) 242 (100), 91(70); HRMS calcd for C$_{16}$H$_{18}$O$_2$: 242.1307. Found: 242.1312.

Methyl trans-4-methyl-3-phenyl-cyclohepta-1,5-diene-1-carboxylate (5)

A solution of (E) Methyl 2-diazo-4-phenyl-3-butenoate (0.26 g, 1.3 mmol) in dry pentane (20 mL) is added dropwise to a stirred solution of Rh$_2$(TBSP)$_4$ (0.0195 g, 13.5 mmol) and cis-1,3-pentadiene (0.45 g, 6.7 mmol) in dry pentane (50 mL) under an argon atmosphere at room temperature. After stirring for 2 hours the solvent is removed under reduced pressure. Purification by silica gel column chromatography (1/99; diethyl ether/petroleum ether, R$_f$=0.05) gave the product as a yellow oil (0.25 g, 79%). IR (neat) 3025.0, 2952.4, 2872.3, 1712.2, 1652.4, 1455.8, 1435.7, 1240.3; $^1$H NMR (CDCl$_3$)d 7.43–7.21 (m, 5H), 7.05 (d, 1H, J=5.1 Hz), 5.82 (dp, 1H, J=5.7, 2.0 Hz), 5.58 (dd, 1H, J=5.3, 3.8 Hz), 3.74 (s, 3H), 3.60 (dd, 1H, J=9.8, 5.2 Hz), 3.29 (d, 1H, J=5.7 Hz), 2.90–5.70 (m, 1H), 0.83 (d, 3H, J=7.0 Hz); $^{13}$C NMR (CDCl$_3$)d 168.0, 146.3, 143.5, 136.7, 131.9, 128.6, 128.2, 126.7, 126.6, 51.9, 51.0, 36.3, 25.3, 20.8; MS m/z (relative intensity) 242 (100), 91 (70); HRMS calcd for C$_{16}$H$_{18}$O$_2$: 242.1307. Found: 242.1314.

Methyl cis-4-tert-butyldimethylsilyloxy-3-phenylcyclohepta-1,5-diene-1-carboxylate (6)

A solution of 2a (0.20 g, 1.0 mmol) in dry pentane (10 mL) is added dropwise to a stirred solution of $Rh_2(TBSP)_4$ (0.0147 g, 10.2 mmol) and (1E)-1-(tert-butyldimethylsilyl)oxy-1,3-butadiene (0.92 g, 5.0 mmol) in dry pentane (60 mL) under an argon atmosphere at room temperature. After stirring for two hours the solvent is removed under reduced pressure. The excess diene was removed by Kugelrohr bulb-to-bulb distillation (35°–45° C. 0.2 mm Hg). Purification silica gel column chromotography (5/95; diethyl ether/ petroleum ether, $R_f$=0.37) gave the product as a yellow oil (0.24 g, 67%). IR ($CHCl_3$) 3358.3, 3019.7, 2915.2, 1447.7, 1303.5, 1096.4; $^1$H NMR ($CDCl_3$)d 7.35–7.18 (m, 5H), 7.04 (d, 1H, J=4.5), 5.90–5.80 (m, 1H), 5.79 (dd, 1H, J=8.8, 2.9 Hz), 4.56 (d, 1H, J=10.2 Hz), 3.76 (dd, 1H, J=4.3, 2.0 Hz), 3.73 (s, 3H), 3.28 (d, 1H, J=5.2 Hz), 0.70 (s, 9H), −0.16 (s, 3H), −0.47 (s, 3H); $^{13}$C NMR ($CDCl_3$) d 168.0, 143.3, 142.1, 136.9, 132.1, 129.2, 128.2, 126.8, 71.5, 52.4, 52.2, 25.7, 25.6, 17.8; MS m/z (relative intensity) 301 (25), 167 (20), 91 (19), 89 (100), 75 (37), 73 (54), 57 (18);

Anal. Calcd for $C_{21}H_{30}O_3Si$: C, 70.35; H, 8.43. Found: C, 70.18; H, 8.38; HRMS calcd for $C_{21}H_{30}O_3Si$: 358.1964. Found: 358.1967.

Methyl 8-(1,1-dimethylethoxycarbonyl)-8-azabicyclo[3.2.1]octa-2,6-diene-2-carboxylate (7a)

A solution of vinyldiazomethane 1a (1.16 g, 9.2 mmol) in dry pentane (100 ml) was added dropwise over 3 h to a solution of N-BOC-pyrrole 8a (7.75 g, 46.3 mmol) and rhodium(II) (S)-N-(4-tert-butylbenzenesulfonyl)prolinate (135.6 mg, 0.094 mmol) in dry pentane (100 ml) heated at reflux under Ar. On completion of the addition, the solution was heated for a further 12 h at reflux. The solvent was removed in vacuo and excess 8a was removed by bulb to bulb distillation. Flash chromatography (0–25% diethyl ether/petroleum ether) gave crude 7a which was further purified by Kugelrohr distillation (105°–115° C./0.5 mm Hg)(1.21 g, 50%): GC analysis on a Chiraldex β-PH cyclodextrin column revealed that 7a was obtained in 51% ee.

Methyl 8-Acetyl-8-azabicyclo[3.2.1]octa-2,6-diene-2-carboxylate (7b)

A solution of vinyldiazomethane 1a (0.34 g, 2.7 mmol) in dry pentane (20 ml) was added dropwise over 30 min to a solution of N-acetylpyrrole 8b (1.49 g, 13.5 mmol) and rhodium(II) (S)-N-(4-tert-butylbenzenesulfonyl)prolinate (38.4 mg, 0.027 mmol) in dry pentane (17 ml) heated at reflux under Ar. On completion of the addition, the solution was heated for a further 30 min at reflux. The solvent was removed in vacuo. Flash chromatography (75–90% ethyl acetate/hexanes) gave the title compound 7b (0.262 g, 46%): $^1$H NMR ($CDCl_3$) δ6.54 (m, 1H), 6.45 (dd, 1H, J=6.0 and 2.6 Hz), 5.94 (dd, 1H, J=6.0 and 2.6 Hz), [5.43 (m)], 4.97 (t, 2H, J=1.1), [4.58 (m)], 3.74 (s, 3H), [3.71 (s)], 2.86 (ddd, 1H, J=20.0, 5.8 and 3.1 Hz) [2.68 (ddd, J=19.5, 5.4 and 2.9 Hz)], [2.07 (dd, J=19.7 and 4.0 Hz)], [2.02 (s)], 1.97 (s,3H), 1.92 (dd, 1H, J=20.0 and 4.0 Hz). GC analysis on a Chiraldex β-PH cyclodextrin column revealed that 7b was obtained in 17% ee.

Methyl 8-Methoxycarbonyl-8-azabicyclo[3.2.1]octa-2,6-diene-2-carboxylate (7c)

A solution of vinyldiazomethane 1a (0.51 g, 4 mmol) in dry pentane (30 ml) was added dropwise over 90 min to a solution of N-methoxycarbonylpyrrole 8c (2.53 g, 20 mmol) and rhodium(II) (S)-N-(4-tert-butylbenzenesulfonyl)prolinate (33.1 mg, 0.02 mmol) in dry pentane (25 ml) heated at reflux under Ar. On completion of the addition, the solution was heated for a further 30 min at reflux. The solvent was then removed in vacuo. Flash chromatography (20–50% ether/pentane) gave the title compound 7c (0.396 g, 44%):$^1$H NMR ($CDCl_3$) 6.46 (m, 1H), 6.43 (dd, 1H, J=5.9 and 2.2 Hz), 5.88 (dd, 1H, J=6.0 and 2.4 Hz), 5.03 (br s, 1H), 4.65 (br s, 1H), 3.70 (s, 3H), 3.63 (s, 3H), 2.79 (br m, 1H), 1.90 (dd, 1H, J=19.8 and 4.0 Hz). GC analysis on a Chiraldex β-PH cyclodextrin column revealed that 7c was obtained in 42% ee.

Methyl 8-Methylsulfonyl-8-azabicyclo[3.2.1]octa-2,6-diene-2-carboxylate (7d)

A solution of vinyldiazomethane 1a (0.25 g, 2.0 mmol) in dry pentane (15 ml) was added dropwise over 30 min to a solution of N-methylsulfonylpyrrole 7d (1.44 g, 10.0 mmol) and rhodium(II) (S)-N-(4-tert-butylbenzenesulfonyl)prolinate (29.3 mg, 0.02 mmol) in dry pentane (24 ml) and dry dichloromethane (6 ml) heated at reflux under Ar. On completion of the addition, the solution was heated for a further 30 min at reflux. The solvent was removed in vacuo., and flash chromatography (silica, 50–80% ether/pentane) of the residue gave the title compound 7d (0.164 g, 34%): $^1$H NMR ($CDCl_3$) δ6.53 (m, 1H), 6.52 (dd, 1H, J=5.8 and 2.1 Hz), 5.92 (dd, 1H, J=5.7 and 2.0 Hz), 5.08 (br s, 1H), 4.68 (br d, 1H, J=5.3 Hz), 3.73 (s, 3H), 2.84 (ddd, 1H, J=19.7, 5.6 and 3.1 Hz), 2.66 (s,3H), 2.06 (dd, 1H, J=19.7 and 4.1 Hz). GC analysis on a Chiraldex β-PH cyclodextrin column revealed that 7d was formed in 29% ee.

For each of the above reactions, the enantiomeric excess, i.e., the percent ee which means the excess amount of one enantiomer or stereoisomer over the other, for example, if a mixture is prepared and there is 75% one optical isomer and 25% of the other, the percent ee is 50%. The percents for each of the above examples are set forth in table 2.

It can be seen from the above that the reaction is highly stereoselective, and particularly where methyl moiety is employed on the vinyldiazomethane substantial enantiomeric excesses are produced. This invention therefore accomplishes at least all of its stated objectives.

What is claimed is:

1. A process of chiral synthesis of optionally substituted cyclohepta-1,5 dienes or optionally substituted 8-aza-bicyclo [3.2.1] octa-2,6 dienes comprising:

reacting a diene of the formula:

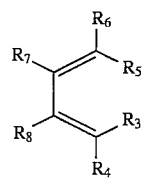

with a vinyldiazomethane of the formula:

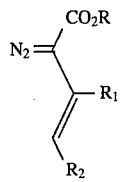

wherein

R is $C_1$ to $C_4$, $R_1$ and $R_2$ are selected from the group consisting of $C_1$ to $C_{20}$ alkyl, phenyl, vinyl, hydrogen, silyloxy, and $R_4$ and $R_6$ are selected from the group consisting of $C_1$ to $C_{20}$ alkyl, $C_1$ to $C_{20}$ alkoxy, acetoxy, and silyloxy, and $R_3$ and $R_5$ may be the same or different and are selected from the group consisting of hydrogen, $C_1$ to $C_{20}$ alkyl, $C_1$ to $C_{20}$ alkoxy, silyloxy, and adjoining moieties nitrogen, oxygen, methylene and ethylene and $R_7$ and $R_8$ may be the same or different, and each may be selected from the group consisting of $C_1$ to $C_{20}$ alkyl, alkoxy, silyloxy and hydrogen, said reaction occurring in a non-polar solvent and in the present of a catalytically effective amount of a chiral di-rhodium(II) tetracarboxylate catalyst, wherein $R_3$ and $R_5$ are an adjoining moiety selected from the group consisting of nitrogen, oxygen, methylene, and ethylene, and further providing that the amount of the rhodium chiral catalyst is from 0.0001 equivalents to 0.1 equivalents of the diazomethane.

2. The process of claim 1 wherein the amount of chiral catalyst is from 0.001 equivalents of the vinyldiazomethane compound to 0.01 of vinyldiazomethane compound.

3. A process of chiral synthesis comprising:

reacting a diene of the formula:

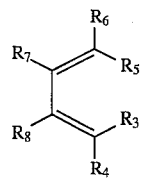

with a vinyldiazomethane of the formula:

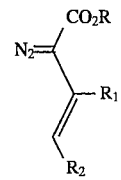

wherein

R is $C_1$ to $C_4$, $R_1$ and $R_2$ are selected from the group consisting of $C_1$ to $C_{20}$ alkyl, phenyl, vinyl, hydrogen, silyloxy, and $R_4$ and $R_6$ are selected from the group consisting of $C_1$ to $C_{20}$ alkyl, $C_1$ to $C_{20}$ alkoxy, acetoxy, and silyloxy, and $R_3$ and $R_5$ may be the same or different and are selected from the group consisting of hydrogen, $C_1$ to $C_{20}$ alkyl, $C_1$ to $C_{20}$ alkoxy, silyloxy, and adjoining moieties nitrogen, oxygen, methylene and ethylene and $R_7$ and $R_8$ may be the same or different, and each may be selected from the group consisting of $C_1$ to $C_{20}$ alkyl, alkoxy, silyloxy and hydrogen, said reaction occurring in a non-polar solvent and in the presence of a catalytically effective amount of a chiral di-rhodium(II) tetracarboxylate catalyst, and further providing that $R_3$ is a —[NH]— joining moiety and $R_3$ and $R_5$ are joined by said joining moiety to form a pyrrole.

* * * * *